United States Patent [19]

Board et al.

[11] Patent Number: 4,530,240

[45] Date of Patent: Jul. 23, 1985

[54] METHOD AND APPARATUS FOR DIAGNOSING MACHINE CONDITION

[75] Inventors: David B. Board, Boca Raton, Fla.; William J. Cooper, King of Prussia, Pa.

[73] Assignee: Diagnostic Equipment Development, Inc., Edgemont, Pa.

[21] Appl. No.: 551,892

[22] Filed: Nov. 15, 1983

[51] Int. Cl.³ ............................................ G01N 29/04
[52] U.S. Cl. .......................................... 73/593; 73/660
[58] Field of Search .................................. 73/593, 660

[56] References Cited

U.S. PATENT DOCUMENTS

| | | | |
|---|---|---|---|
| 3,554,012 | 1/1971 | Sohoel | 73/593 |
| 3,842,663 | 10/1974 | Harting et al. | 73/593 |
| 4,429,578 | 2/1984 | Czechowski | 73/660 |

Primary Examiner—Anthony V. Ciarlante
Attorney, Agent, or Firm—Robert K. Youtie

[57] ABSTRACT

For use in predicting machine failure a transducer sensor, such as piezoelectric crystal, is applied to a machine for sensing machine motion and structure borne sound, including vibration friction, and shock waves. The structure borne sound and motion sensed is converted to electrical signals which are filtered to leave only the friction and shock waves, which waves are processed, as by detecting the envelope and integrating beneath the envelope, resulting in a measure of friction and shock wave energy. This measure may be compared with that of a less used machine, say the same machine when new, to indicate the rise in energy due to change in machine parts.

4 Claims, 3 Drawing Figures 4,530,240

METHOD AND APPARATUS FOR DIAGNOSING MACHINE CONDITION

BACKGROUND OF THE INVENTION

This invention is concerned with predicting the maintenance necessary on machinery. Heretofore it has been conventional to schedule machine maintenance by period of use, but this may result in much unnecessary maintenance and down time on machines requiring no maintenance. Another common method for scheduling maintenance is that by analysis of used lubricant, but this may be expensive, involve substantial time for processing the lubricant, and may indicate only one of many parts being worn.

Also commonly employed to indicate the need for machine maintenance is vibration analysis. However, this method does not distinguish between systemic vibration and that resulting from small defects, but may obscure the latter. There have been attempts to detect machine defects by picking up and analyzing vibrational waves, but these have not proved satisfactory. They tend to cause false alarms resulting in unnecessary maintenance, and on the other hand to mask defects prior to machine failure.

Among the prior patents of this type, of which applicant is aware, are those listed below:

| U.S. PAT. NO. | PATENTEE |
| --- | --- |
| 3,554,012 | Sohoel |
| 3,712,130 | Weichbrodt et al. |
| 4,007,630 | Noda |

SUMMARY OF THE INVENTION

It is an important object of the present invention to provide a method and apparatus for accurately predicting need for maintenance in rotary equipment, for example equipment including gears and bearings.

It is another object of the present invention to provide a method and apparatus for detecting damage or defects in machines, which requires relatively little energy and can detect relatively small defects, minimizes the possibility of both false alarms and undetected failures, while indicating with relatively high accuracy the defective part or parts.

It is another object of the present invention to provide machine fault detection immediately, as well as affording a profile of fault progression, all without parts removal or shutdown.

Still another object of the present invention resides in the provision of a method and apparatus for testing machinery to assure its compliance with specifications and in settling warranty claims.

Other objects of the present invention will become apparent upon reading the following specification and referring to the accompanying drawings, which form a material part of this disclosure.

The invention accordingly consists in the features of construction, combinations and arrangement or parts and method steps, which will be exemplified in the following description, and of which the scope will be indicated by the appended claims.

DESCRIPTION OF THE PREFERRED EMBODIMENT

Figure 1:
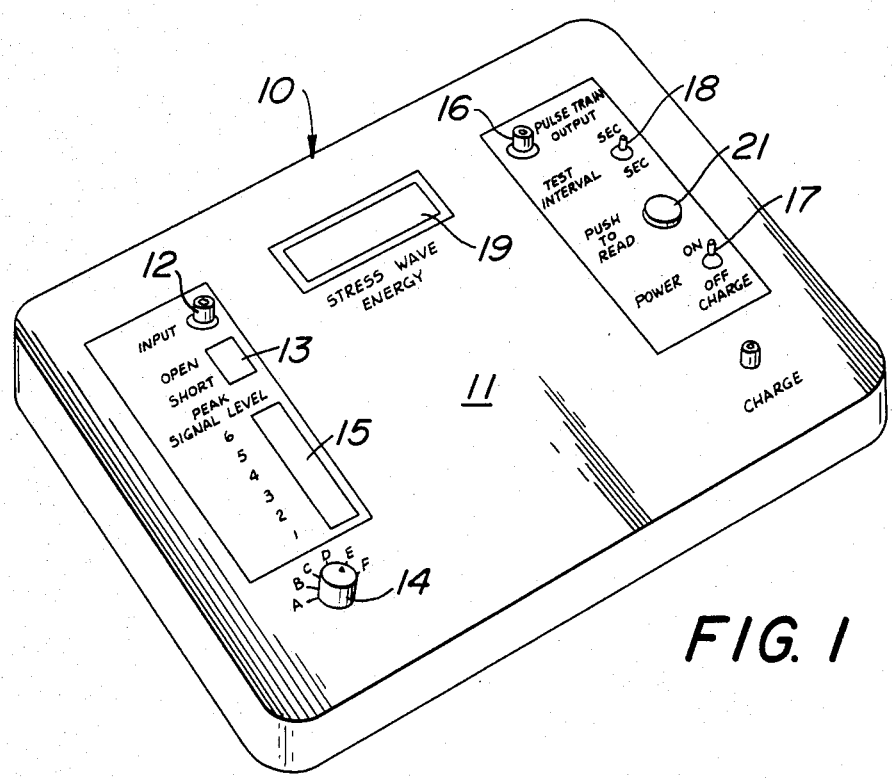
FIG. 1 is a top perspective view showing a diagnostic device of the present invention.

Referring now more particularly to the drawings, and specifically to FIG. 1 thereof, a case is generally designated 10 containing the necessary circuitry for the instant invention and having a face plate 11 provided on one side of the case. The face 11 is provided with various indicators, controls, and jacks. For example, an input jack 12 for connection to a transducer. An input status detector is shown at 13 for indicating the input circuit as "open" or "short", as by L.E.D.'s or the like.

A gain selector switch 14 is used to control sensitivity, and may be associated with peak signal level indicators, as at 15.

An output jack 16 is provided on the case 10. Also provided is a power switch 17, and an integrating interval switch 18. The integral to be read, or a numerical measure thereof as will appear more fully hereinafter, is indicated by the readout 19.

Figure 2A:
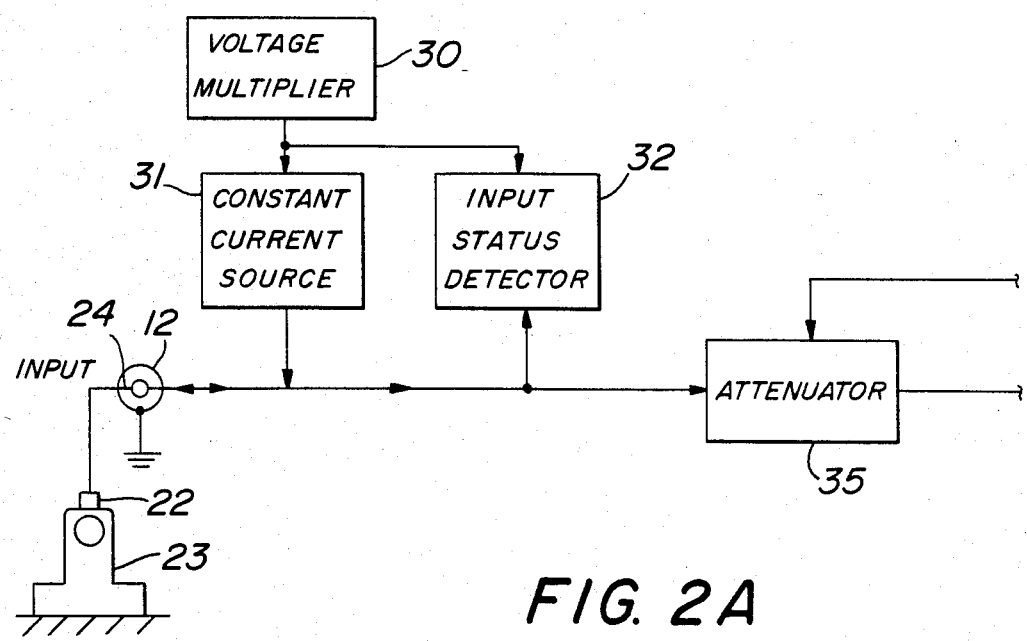
FIGS. 2A and 2B is a block diagram of apparatus used in practice of the present invention.
Figure 2B:
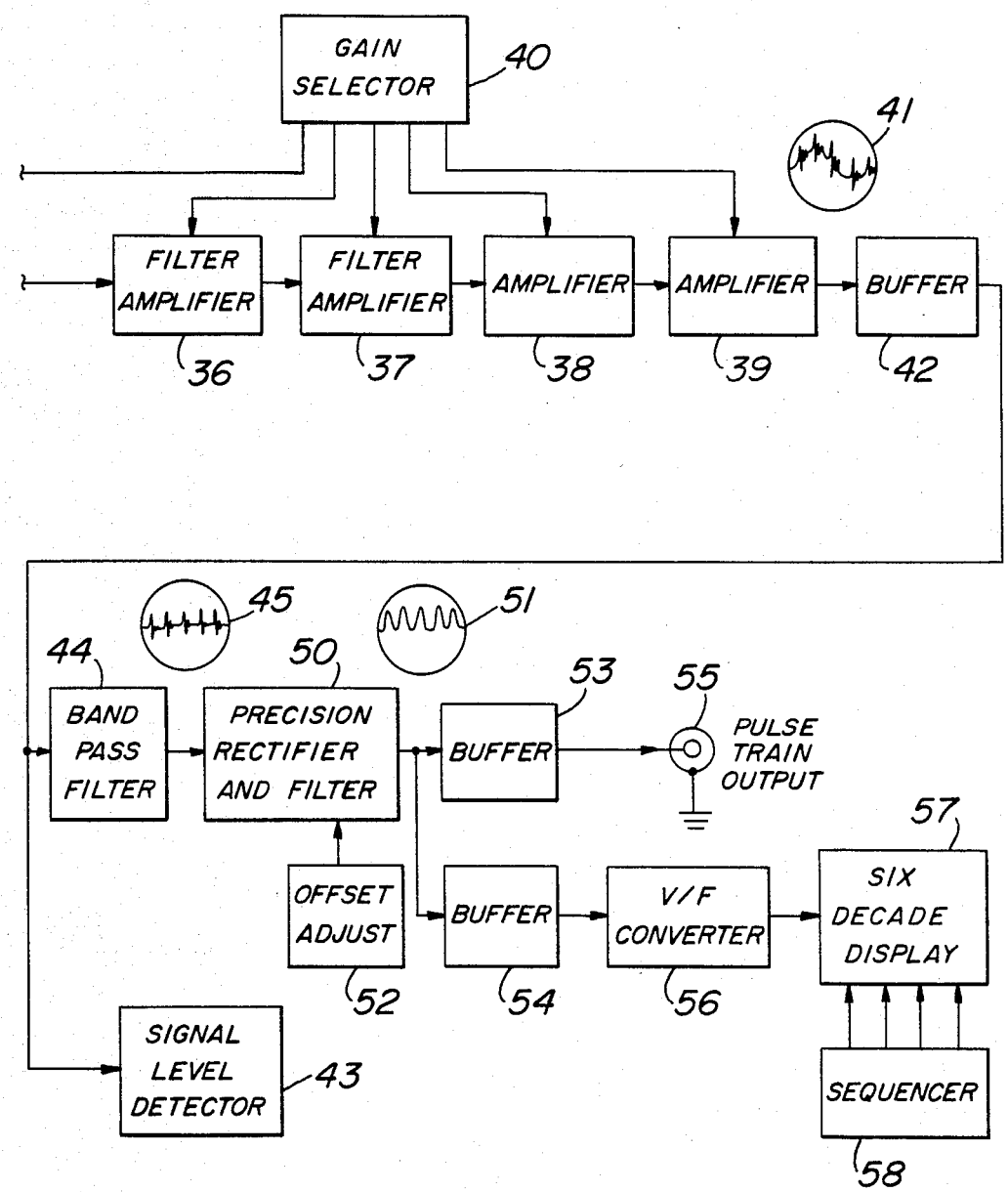

Referring now to FIG. 2, the input 12 is connected to a suitable transducer, one such being a piezoelectric crystal which is mounted to the structure of a machine being tested by firm clamping thereto or other affixation. A crystal 22 is illustrated as applied to a machine or apparatus 23, shown for purposes of illustration and simplicity as a pillow block 23. The transducer 22 is connected through a jack 24 to the input 12, and the sensor may be suitably buffered, as by an FET.

A voltage multiplier, designated 30, may be employed to supply a desired voltage from a battery source to a constant current source 31. The current source 31 supplies the constant current to the built-in amplifier of the transducer crystal 22.

Monitoring the condition of the transducer 22 and its connecting cable is an input status detector 32.

In practice, the voltage multiplier 30 may supply a constant 18VDC, from a nominal 9 VDC battery source, the current source 31 supplying a constant 2 milliamp to power the transducer crystal.

The input status detector 32 may compare the multiplier voltage to ground for detecting open and short circuits, for indication by L.E.D.'s 13 for annunciating these fault conditions.

The sensor or transducer 22 will convert motion of machine 23 to electrical signals, specifically converting to electrical signals both the elastic machine vibration and the transient, structure borne sound waves resulting from friction and shock of machine defects. The vibrational oscillations are of relatively low frequency, below 20 khz, while the friction and shock wave frequencies are relatively high, above 20 khz. The sensing crystal 22 is selected to have a resonant frequency in its operative mounted condition adequately far from the natural frequency of the machine 23 so as not to be excited by the natural machine frequency. It has been found that a crystal resonant mounted frequency of about 34 khz is satisfactory, such that the crystal is effectively excited at its natural resonant frequency by the machine defects rather than vibration of the machine.

The sensor signal is passed to the series of attenuator 35, first stage filter amplifier 36, second stage filter amplifier 37, third stage amplifier 38 and fourth stage amplifier 39. A gain selector 40 is connected to the several attenuator 35 and amplifier stages 36–39 for selective switching in and out of the attenuator and amplifier stages. The gain selector switch 14 in FIG. 1 operates the gain selector 40 in FIG. 2 to successively switch out the attenuator 35 and switch in each additional amplifier stage 36–39. The adjustable sensitivity provides a 75 db range of sensitivity adjustment, each of the five stages having a gain of 15 db. By this gain selection the apparatus is usable with a wide range of transducer signals, the attenuator being inserted for high amplitude transducer signals and out of circuit for lesser signals, while increasing numbers of amplification stages being in circuit for transducer signals of decreasing amplitude.

In addition, the early amplification stages 36 and 37 are advantageously provided with band pass filtering around the sensor's mounted resonant frequency. This early filtering out of signals other than in the region of the transducer's resonant frequency allows greater subsequent gain of the band of passed signals by later amplification stages 38 and 39.

A representative wave form leaving the amplifier 39 is shown at 41, the transients indicating frictional and shock waves.

This amplifier signal output 41 is buffered, as by a buffering circuit 42 and then supplied to both a signal level detector 43 and band pass filter 44. The signal level detector includes a comparator network indicating the peak amplitude of the signal level which may be displayed by the L.E.D.'s 15 on the panel 11. The L.E.D.'s 15 may be 6 in number and serve to display the peak amplitude in increments of 6 db. Thus, an operator may set switch 14 to control gain selector 40 to cover a broad range of machines being tested.

The buffered signal output is also fed to band pass filter 44. This filter may include three adjustable gain and peaking sections that allow the overall response of the filter amplifiers 36 and 37, together with the filter 44 to have a flatness of less than ±0.5 db from 30 khz to 38 khz with an attenuation of greater than 40 db at 20 khz and 45 db at 60 khz. This signal, which may typically assume a wave form 45, is the output of the stress wave (friction and shock wave) sensed by the sensor at its mounted resonant frequency.

This wave form 45 is isolated from systemic machine vibration and derives essentially from friction and shock waves, which may be called stress waves.

For calibration of the apparatus in the top 80% of its linear dynamic range, the band pass filter 44 may have its gain stages adjusted, as required.

A precision rectifier and filter 50 may receive the signals of wave form 45 from filter 44. Full wave rectification is performed in block 50 for maximum signal information retrieval. The rectifier is combined with a low pass filter in block 50 to perform as an energy discriminator for true envelope detection of the stress wave signal resulting in a typical rectified envelope wave form 51 of the stress wave signal.

Connected to the rectifier and filter 50 is an offset adjustment circuit 52 which permits of apparatus calibration of signals in the lower 20% of the instrument's linear dynamic range.

The wave form 51 is applied to buffering circuits 53 and 54 for isolation from the rectifier and filter 50. From the buffer 53, the signal may pass to an output jack 55, as for display on a CRT, for spectrum analysis, or other.

However, for the advantages of digital readout, the low pass filtered signal 51 may be buffered at 54 and applied to a voltage to frequency converter 56. The low pass filtered signal 51 is suitably within the linear frequency response range of the converter 56; and, the output of the converter is applied to a counter 57 for integration under the envelope. That is, the counter 57 may include a six decade display, such as the digital readout 19 of the panel 11, and is associated with a sequencer 58 so that the display provides a time interval integration of the stress wave form 51. The test interval may be selected by switch 18 on the panel 11.

This integration of the stress wave form 51 is a measure of the energy of the stress wave form, which indicates the severity of a defect. For example, in a spalled bearing, the size and area of the spall would be generally proportional to the energy measured by integrator 57.

After the selection of a test interval, as by positioning of switch 18, the "PUSH TO READ" button 21 will cause the readout 19 to count up and display the number, which will remain during the following integration period, after which it will be updated and the procedure repeated.

From the foregoing, it is seen that the present invention provides a method and apparatus for diagnosing machine condition and predicting failure, which method and apparatus are extremely simple to use, efficient and accurate in results, and otherwise fully accomplish their intended objects.

Although the present invention has been described in some detail by way of illustration and example for purposes of clarity of understanding, it is understood that certain changes and modifications may be made within the spirit of the invention.

What is claimed is:

1. Apparatus for predicting failures in rotary equipment including bearings, gears and the like, said apparatus comprising: a transducing sensor for attachment to the equipment to produce electrical signals corresponding to vibration and friction and shock waves in the equipment; band pass filter means connected to the sensor for filtering out the signals corresponding to vibration and passing only signals corresponding to friction and shock waves in a frequency band around the natural frequency of said sensor; detector means connected to said filter means for detecting the envelope of signals in said frequency band; integrating means connected to said detector means for integrating the envelopes of said friction and shock signals as a measure of friction and shock wave energy; and full wave rectifier means between said band pass filter means and detector means, for maximum information utilization, said integrating means comprising voltage to frequency converter means connected to said detector means, and counter means connected to said voltage to frequency converter means.

2. Apparatus for predicting failure in rotary equipment including bearings, gears and the like, said apparatus comprising: a transducing sensor for attachment to the equipment to produce electrical signals corresponding to vibration and friction and shock waves in the equipment; band pass filter means connected to the sensor for filtering out the signals corresponding to vibration and passing only signals corresponding to friction and shock waves in a frequency band around the natural frequency of said sensor; detector means connected to said filter means for detecting the envelope of signals in said frequency band; integrating means connected to said detector means for integrating the envelopes of said friction and shock signals as a measure of friction and shock wave energy, said integrating means comprising voltage to frequency converter means connected to said detector means, and counter means connected to said voltage to frequency converter means.

3. The method of diagnosing machine wear comprising the steps of: sensing machine motion including (a) vibration and (b) friction and shock waves; converting the motion sensed to electrical signals; filtering out the vibration signals to leave friction and shock waves signals; and integrating the friction and shock wave signals to obtain a measure of friction and shock wave energy, for comparison with a measure of friction and shock wave energy of a less used machine, wherein said integrating is by voltage to frequency conversion and counting.

4. The method of diagnosing machine wear comprising the steps of: sensing machine motion including (a) vibration and (b) friction and shock waves; converting the motion sensed to electrical signals; filtering out the vibration signals to leave the friction and shock wave signals; integrating the friction and shock wave signals to obtain a measure of friction and shock wave energy, for comparison with a measure of friction and shock wave energy of a less used machine; filtering out frequencies of said friction and shock wave signals except in the region of the natural frequency of the sensor used to pass a frequency band of said friction and shock wave signals; rectifying the signals of said frequency band; and detecting the envelope of said rectified signals for integration of the envelope, wherein said integrating is by voltage to frequency conversion and counting.

* * * * *